United States Patent [19]

Pfirmann et al.

[11] Patent Number: 5,773,651
[45] Date of Patent: Jun. 30, 1998

[54] PROCESS FOR THE PREPARATION OF FLUORINE-CONTAINING CHEMICAL COMPOUNDS

[75] Inventors: Ralf Pfirmann, Griesheim; Friedrich Seitz, Eschborn, both of Germany

[73] Assignee: Hoechst Aktiengesellschaft, Germany

[21] Appl. No.: 753,714

[22] Filed: Nov. 27, 1996

[30] Foreign Application Priority Data

Dec. 1, 1995 [DE] Germany .................. 195 44 871.5

[51] Int. Cl.⁶ .......................... C07C 62/06; C07C 205/00
[52] U.S. Cl. .......................... 562/466; 562/490; 562/493; 562/456; 568/938; 568/937; 568/709
[58] Field of Search ...................... 562/466, 490, 562/493, 450; 568/709, 938, 937

[56] References Cited

U.S. PATENT DOCUMENTS

| 4,496,621 | 1/1985 | Hubert et al. . |
| 4,607,959 | 8/1986 | Miyazaki et al. . |

FOREIGN PATENT DOCUMENTS

| 0 310 561 | 4/1989 | European Pat. Off. . |
| 2 046 709 | 3/1972 | Germany . |
| 25 11 381 | 9/1976 | Germany . |
| 33 19 296 | 12/1983 | Germany . |
| 1507722 | 4/1978 | United Kingdom . |
| 1330485 | 11/1982 | United Kingdom . |

OTHER PUBLICATIONS

Römpp, *Chemie–Lexikon* [*Chemical Dictionary*], 5th Ed., vol. 1, p. 1125 (1962).
Künzel, *Chemie–Technik 17*:(12), 16, 18, 20 & 21 (1988).
Künzel, *VDI Berichte* 674:87–103 (1988).
Böder, H., et al, *Chem.–Ing.–Tech 59*:(2), 122–126 (1987).
Würmseherm H., et al, *Swiss Chem 5*: (10a), 71–25 (1983).
Hart, G. L., et al, *Carbon Fibres*, 2nd int. conf., London, Feb. 18–20, paper 34 (1974).
Boeder, H., et al, *Composite Polymers 1*:(6), 445–455 (1988).
Lally, K.S., et al, *Chemical Engineering Progress 84*:(11), "Structural Composite Mixers", Index p. (1988).
*Chemical Engineering 93*:(10), p. 47 (1986).
*Ullmann's Encyclopedia of Industrial Chemistry*, 5th Ed., vol. 5A, 1986, pp. 539–544.

*Primary Examiner*—Paul J. Killos
*Attorney, Agent, or Firm*—Connolly and Hutz

[57] ABSTRACT

Process for the preparation of fluorine-containing compounds by reduction in a container provided with a stirrer, the stirrer being constructed entirely or partly of a carbon material.

15 Claims, 1 Drawing Sheet

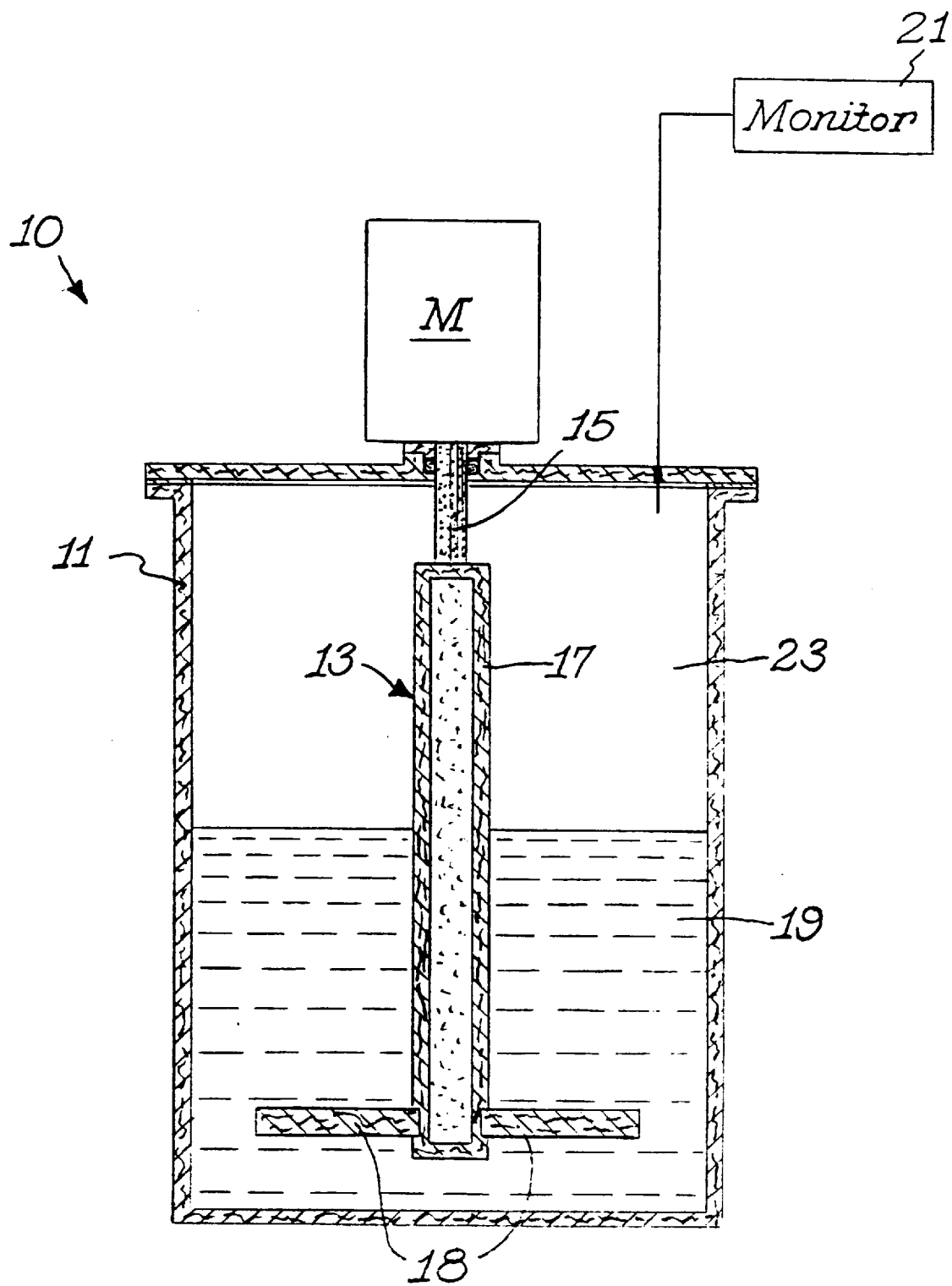

PROCESS FOR THE PREPARATION OF FLUORINE-CONTAINING CHEMICAL COMPOUNDS

Processes for the preparation of fluorine-containing compounds are distinguished by the fact that very severe corrosion by hydrogen fluoride sometimes occurs, especially in acid media. As a result, further corrosion caused by other influences is intensified. Furthermore, the passive layer on metals is destroyed by the presence of fluoride ions, so that corrosion by other constituents of the mixture is also facilitated as a result. This prevents the use not only of stainless steel fittings, but also of enamel fittings, since enamel undergoes severe removal of material due to the formation of hexafluorosilicic acid, and the rate of removal sharply increases progressively as corrosion starts.

As a rule, a change is made to polyethylene (PE) apparatuses or correspondingly lined apparatuses at low temperatures, i.e. to about 60° C. The use of polytetrafluoroethylene (PTFE) is also possible up to temperatures of 100° C. to about 160° C., but is already associated with considerable problems. Thus, special constructions, especially in the heat exchange and stirrer region, must be used at temperatures above 120° C. In cold parts of the apparatus, it is also possible to use components of polyvinylidene fluoride (PVDF), which indeed is easier to process than PTFE but has a significantly lower softening point and is therefore severely limited in its range of use, especially for components exposed to high mechanical stresses, such as stirrer devices. High torques in particular, which occur when stirrers are started up, lead to deformations because of a lack of torsion resistance.

Other fluorine plastics (for example Fluoroshield®) are likewise resistant in principle to acid media containing hydrogen fluoride. However, these plastics (PTFE, PVDF, Fluoroshield) have, inter alia, the following disadvantages. On the one hand, the heat transition coefficients of these plastics are so low compared with conventional materials, such as, for example, metals, that it is necessary to keep the wall thicknesses low. Because of the mechanical properties of these plastics (flow properties on approaching the softening point, compressive, tensile and shear strengths, torsion resistance), the apparatuses cannot be produced from massive material, and the plastics can only be used for lining or have to be sintered on. On the other hand, the materials are not resistant to diffusion of organic compounds, and above all to diffusion of hydrogen fluoride, because of the lipophilic properties and their generally low density. This means, however, especially in reactions under pressure or at a higher temperature, facilitated by the low wall thicknesses because of the low heat transition coefficients and technical circumstances, that as a rule corrosion by hydrogen fluoride or hydrofluoric acid (in particular local corrosion phenomena) on metallic external containers rapidly occurs after the apparatuses have been started up. In spite of the generally low wall thicknesses, apparatuses coated with plastic are only an unsatisfactory solution, since the heat transition coefficients are so low that nevertheless no exothermal or endothermal reactions can be carried out, since the heating or cooling achieved is only poor. Further disadvantages of the fluorine polymer materials are the poor processability and the limitation to processes under normal and under increased pressure, since the use of reduced pressure is scarcely possible because the layers detach from the external containers, because of their low adhesion, and deform irregularly.

Under the reaction conditions which often occur, especially in aqueous solutions, hydrofluoric acid is always in the vapour space, or even acid-containing steam has to be condensed when the reaction gas is let down. However, corrosion by condensing dilute hydrofluoric acid can scarcely be controlled by conventional methods.

There is therefore a need for a simple and universally applicable process which, in addition to allowing conventional reactions, also allows reactions which comprise hydrogen fluoride in the reaction mixture, especially in aqueous solutions.

According to Römpp, Chemie-Lexikon [Chemical Dictionary], 5th Edition 1962 (Volume 1, page 1125), Diabon® is an acid-resistant material of porous graphite which has been rendered impermeable to liquid by impregnation with resins. This material is resistant to hydrogen fluoride and other mineral acids.

Indications that the use of containers of carbon-containing materials offers advantages, since mechanical strength, good heat transition properties and high corrosion resistance coincide, are also to be found in the following literature:

J. Künzel, Chem.-Tech. (Heidelberg), 17 (12), 16, 18, 20 (1988);

J. Künzel in VDI-Berichte 674, 87–103 (1988);

H. Böder, E. von Gellhorn, J. Künzel, Chem.-Ing.-Tech. (1987) 59 (2), 122–126;

J. Künzel, A. Swozil, H. Würmseher, Swiss Chem. (1983) 5 (10a), 17/22;

G. L. Hart, G. Pritchard, in Carbon Fibres, 2nd int. conf. Proc. London, Feb. 18–20, 1974, paper 34;

J. Künzel, E. von Gellhorn, H. Böder, in Composite Polymers, 1 (6) (1988),

K. S. Lally, W. C. Webster, R. N. Salzman, Chem. Engng. Prog. 84 (11) (1988),

Chem. Engng. 93 (10) (1986), 47.

The invention relates to a process for the preparation of fluorine-containing compounds by reaction in a container provided with a stirrer, which comprises using a stirrer which is constructed entirely or partly of a carbon material.

BRIEF DESCRIPTION OF THE DRAWING

The sole FIGURE of the Drawing is a cross-sectional, front elevational view illustrating a typical apparatus used in the process of this invention.

The stirrer organs of the stirrer used in the process according to the invention are made of carbon-containing material. In contrast, the stirrer shaft of the stirrer can also be made of metal, but it is also possible for this shaft likewise to be made of carbon-containing material. This material can be filled, i.e. pressed, sintered or shaped to a solid workpiece in another manner, with phenolic, epoxy, polyimide or polyester resins or also with fluorine plastics. Fillers which are used for the carbon material are, as a rule, furan resins or phenolic resins or fluorine plastics, for example CTFENDF (poly(chlorotrifluoroethylene-co-vinylidenefluoride)), PTFE (polytetrafluoroethylene), ECTFE (poly(ethylene-co-chlorotrifluoro-ethylene)), ETFE (poly(ethyiene-co-tetrafluoroethylene)), FEP (poly(tetrafluoroethylene-co-hexafluoropropylene)), PCTFE (polychlorotrifluoroethylene), PVDF (polyvinylidene fluoride), PVF (polyvinyl fluoride), TFB (polytetrafluoroethylene-co-hexafluoropropylene-co-vinylidene fluoride)) or CM-X (poly(hexafluoroisobutylene-co-vinylidene fluoride)). Other possible fluorine plastics are, for example, any desired copolymers of hexafluoroisobutylene, hexafluoropropylene, tetrafluoroethylene, vinyl fluoride and vinylidene fluoride or analogous compounds.

These fluorine polymers can furthermore be employed in all instances where PTFE or PVDF are mentioned.

The stirrer shaft of the stirrer can preferably be made of carbon fiber-reinforced plastic (CFP) or of carbon fiber-reinforced carbon (CFC). The carbon fibers in this material in general have a diameter of about 1 to about 100 $\mu$m, preferably about 3 to 30 $\mu$m, in particular 5 to 15 $\mu$m, the fiber content in CFP plastics being about 30 to 90%, preferably 50 to 70%. The fibers are preferably high-modulus or high-strength fibers, it being possible for the fibers to assume angles with respect to one another of 0° to 45°. Fiber composite materials can also be employed. The carbon fibers can also be in the form of corresponding filaments. The CFP and CFC materials in general have flexural strengths of about 50 to 2000 N/mm$^2$, preferably 80 to 1500 N/mm$^2$, in particular 100 to 800. The values for the modulus of elasticity (in tension) are about 10,000 to 400,000 N/mm$^2$, preferably about 25,000 to 130,000 N/mm$^2$, and the tensile strength is about 0.05 to 8, preferably about 0.3 to 1 N/mm$^2$. The density of these materials is about 1.2 to 2.0, preferably 1.55 to 1.6 g/cm$^3$.

Examples which may be mentioned of fibers or fiberwoven materials for reinforcing plastics are the products Sigrafil C40, SFC 6 or 12 or Sigratex (various types) or 320. The corresponding material and technical data can be found, for example, in the technical information sheets from SGL Carbon.

Construction materials which are also possible are the SIGRABOND® types of SGL Carbon, which are available both as CFC (carbon fiber-reinforced carbon) and as CFP (carbon fiber-reinforced plastic). These can also be coated with ceramic materials, such as, for example, SiC. Thus, the types CC 1001 G and CC 1501 G (both CFC) in each case in uncoated form and coated with silicon-infiltrated silicon carbide or α-SiC, and as CFT CC 1506 G, have been tested. Technical data can be found in the corresponding information sheets.

The possible CFP materials can comprise the putties described below or can be filled with epoxy, phenolic or furan resins or with fluorine plastics, such as, for example, polytetrafluoroethylene (PTFE). The polymer matrix of such CFP materials can comprise unsaturated polyesters, phenolic resins, epoxy resins or polyimide resins, thermosetting resins being preferred.

The shaft of the stirrer construction (carbon material) is as a rule made of massive material or is a hollow tube construction, which can optionally be filled with a core of mechanically resistant material, for example metals such as the materials 1.4571 and 2.4610 can be incorporated, in massive form or as a hollow tube as a core of the shaft. If desired, such hollow constructions can be sealed off with the putty materials described below to prevent corrosion on the inside and outside. Since these constructions as a rule are attached to a construction which operates the stirrer and is made of metal, as a rule material No. 1.4571, this transition point is to be sealed off in particular by means of the possibilities described.

The stirrer geometry of the stirrer used can be designed according to all the industrially known variants (cf. inter alia, M. Zlokarnik, H. Judat in Ullmann's Encyclopedia of Industrial Chemistry, Volume B2 (1992), Chapter 25). Thus, single- and multi-stage stirrers are possible. Blade stirrers, cross-beam stirrers, anchor stirrers, impeller or propeller stirrers, turbine and anchor stirrers or also special embodiments of these types, such as, for example, MIG® or INTERMIG®, which ensure particularly intensive thorough mixing while simultaneously optimizing energy consumption can be used (blade, cross-beam and anchor stirrers are preferred). For special problems, for example very viscous reaction mixtures, the technical solutions mentioned in the literature stated are likewise possible. The size and shape of the stirrer organs can be adapted to suit the particular requirements of the reaction apparatus and of the reaction.

The length of the stirrer shaft depends on the size of the reactor and is in general 50 to 95%, in particular 70 to 90%, of the reactor height. The diameter of the stirrer shaft is approximately 1 to 100 cm, the following values specifically being customary: 1 to 4 cm in laboratory units, 5 to 30 cm in pilot plants, 40 to 100 cm in production plants. The particular material of the stirrer shaft depends on whether the stirrer shaft is hollow or massive. In the case of hollow shafts, the material thickness is 2 to 20%, preferably 5 to 15%, based on the total diameter of the shaft. The same applies to the stirrer organs.

The radial dimensions of the stirrer organs depend on the container in which the stirrer is to be employed. The stirrer organs are usually constructed such that they make up 10 to 90, preferably 30 to 80% of the container diameter. The height of the stirrer organs depends greatly on the stirrer type and is about 3 to 20% of the height of the container.

A stirring device sealed off to the outside by an axial face seal, magnetic coupling or stuffing box seal is preferably used according to the invention. These components are used in the usual constructional manner. An essential constituent of such a seal via slip rings is the use of ceramic, corrosion-resistant slip ring materials, such as, for example, boron nitride, boron carbide, silicon nitride or silicon carbide, since these have the required hardness and therefore abrasion resistance. These materials can be employed in various variants, thus, for example, by varying the production process (different sintering, particle size) or by varying the constituents of the material (for example non-stoichiometric contents of the components in the material, such as in silicon-infiltrated silicon carbide), which allows adaptation of the actual properties of the materials to the chemical and mechanical requirements.

As a result of the mode of construction, the stirrer according to the invention has advantages in respect of the resistance of the material, compared with other corrosion-resistant materials, such as, for example, fluorine plastics.

In the process according to the invention, not only the stirrer by itself but in addition also the container for the reaction can be made of the carbon-containing material or be lined with this material. This means that either the components for the container can be made of this material in massive form, or that only the surface is coated with these materials. It is essential here that those components of the container which come into contact with the product are made of the carbon-containing materials or coated with them.

As is known from the literature, graphite produced by special processes, such as, for example, carbonization, has extremely high compressive and tensile moduli. Furthermore, the material is largely resistant to diffusion, especially since, as explained above, corresponding wall thicknesses are no problem at all. The container wall thicknesses which are advantageous in the use according to the invention can be between about 5 and about 200 mm, in particular between about 20 and about 80 mm.

For sealing and jointing and for protecting non-inert components in stirrers and containers, the materials which are customary for this and are filled with organic resins, such as, for example, epoxy, melamine, furan, alkyd, vinyl, polyester, urethane or phenolic resins, are used. Asplit® types are specifically appropriate here, in particular the types CV, CL, CN, ET, OC, OQ and FN, and acid-resistant putties HB, HES HB and HFR, or fireproof putties K12, K14 and K16. However, analogous types of these resins which are commercially available under other names can also equally be used. Explanations on the precise composition of such putties, in particular putties with organic binders, are to be found in Ullmann's Encyclopedia of Industrial Chemistry, Volume 5A 5th, (1986), pages 539 to 544. The commercially available putties Asplit CN, a putty of the phenol-formaldehyde resin type, and Asplit FN, a putty of the furan resin type, are preferred, but modification to other types is appropriate, depending on the nature of the reaction medium. This can be explained well by the example of these two Asplit types, type CN in fact having advantages in the acid range and Asplit FN in the alkaline range, the two types being approximately equivalent in resistance to solvents.

In addition, it is also possible to protect sealing points or components which are not inert per se by layers of inert material, in particular by noble metals, such as gold or platinum. It is likewise possible for such components which are at particular risk to be produced massively from noble metals. The metal layers can be plated on, melted on, sintered or vapor-deposited.

The process according to the invention can be employed in particular for the preparation of organic fluorine compounds. These include both aliphatic and aromatic fluorine compounds, such as, for example, tri- or tetrafluoropropane-carboxylic acid, 2,3,4,5-tetrafluorobenzoic acid, 5-fluoro-2-nitrophenol or similar compounds. Synthesis or working up steps on fluorine-containing compounds in which these compounds are handled in acid, in particular in strongly acid, solutions, especially at elevated temperatures, are particularly preferred. In these process steps, it is found that small amounts of fluoride are always split off from the organic material and give rise to corrosion. The process according to the invention is also beneficial in the case of compounds which also contain chlorine, in addition to fluorine, and where chloride ions or HCl, which likewise have a corrosive action, are liberated analogously. The total concentration of halides in the reaction batch can be 5 ppm to 25%.

The process according to the invention is preferably applied to fluoro-aromatic compounds as reactants or as products, in particular to fluoro-aromatic carboxylic acids and/or phenols, alcohols or functional derivatives thereof, such as esters, amides, halides, aldehydes, benzyl alcohols, ethers, benzyl halides, preferably benzyl fluorides, benzal halides, preferably benzal fluorides, and benzotrihalides, preferably benzotrifluorides, which furthermore contain acid or basic groups. Specifically, the process according to the invention can be used, for example, for the preparation of the following compounds:

Tetrafluorophthalic acid, 2,3,4,5-tetrafluorobenzoic acid, 3-hydroxy-2,4,5-trifluorobenzoic acid, 4-hydroxy-2,3,5-trifluorobenzoic acid, 4-amino-3,5,6-trifluorophthalic acid, 2,3-dichloro-4,5-difluorobenzoic acid, 3-amino-2,4,5-trifluorophthalic acid, 4-chloro-3,5,6-trifluorophthalic acid, 3-chloro-2,4,5-trifluorobenzoic acid, 4-hydroxy-3,5,6-trifluorophthalic acid, 3,5,6-trifluorophthalic acid, 2,4,5-trifluorobenzoic acid, 2-chloro-4,5-difluorobenzoic acid, 2-chloro-6-nitrophenol, 2-chloro-3-fluoro-6-nitrophenol, 5-fluoro-2-nitrophenol and 2,3-difluoro-6-nitrophenol.

The process according to the invention includes, in particular, the following reaction types: halogen-alkoxide exchange, halogen-hydroxide exchange, halogen-amine exchange (in each case in particular exchange of fluorine atoms), halogen-halogen exchange, decarboxylation, decarbonylation, hydrolysis of nitriles, amides, anhydrides, esters, acid chlorides and imides, Schiemann and Balz-Schiemann reaction, Bamberger rearrangement, etherification and acylation, in particular in liquid hydrogen fluoride, which can optionally contain water.

The processes according to the invention can be carried out in aqueous solution and in solutions in the customary organic solvents, aqueous solutions being preferred. The viscosity of the reaction mixture is approximately 0.1 to 5,000 cP, preferably 1 to 1,000 cP, in particular 25 to 250 cP. The speed of rotation of the stirrer is in general 1 to 2,000 revolutions per minute, 100 to 1,000 rpm in laboratory processes, 5 to 200 rpm in pilot plants and 2 to 100 rpm in production plants.

The process according to the invention can be carried out in containers of about 0.5 l (laboratory scale) up to about 20 m$^3$, and plants of medium size which comprise reaction units of about 200 l to about 5 m$^3$ are preferred.

The process can be carried out according to the invention at temperatures between about −20° and about 220° C., preferably between 500° and 180° C., in particular at 100° to 180° C. The possible pressures are 0.05 to 4.0 MPa, preferably 0.1 to 2.0 MPa.

The use of the apparatuses to be employed according to the invention is particularly advantageous if non-purified reaction mixtures are to be further processed, since these can comprise higher amounts of free fluoride. This may be the case in particular if functionalizations are carried out by nucleophilic exchange reactions on organic, aliphatic or aromatic compounds, if these functionalizations liberate fluoride ions per se and the mixtures have to be acidified for working up or further processing, as occurs in the synthesis of phenols or special carboxylic acids. As a result, a purification step can be spared in each case, which means that possible losses in yield are prevented and production costs are also saved.

It goes without saying that the process according to the invention is limited to working with non-oxidizing media, since the carbon-containing material is attacked by oxidizing agents. This means that, in particular, reactions with sulfuric acid with a content of more than 70% or with halogens, such as chlorine or bromine, or with hydrogen peroxide are subject to limitations. However, exceptions are entirely possible at very low temperatures, i.e. in general at temperatures below about 40° C.

It is a great advantage of the process according to the invention that the materials used, if they are not absolutely inert per se under the reaction conditions in question, are of a nature such that their wearing away, removal of material or change in the surface does not have an accelerating effect on further corrosion.

These materials thus essentially contrast with metallic materials or enamel, which always show a progressive tendency towards corrosion when attack starts, if only due to the increase in surface area.

The process according to the invention, employing a special stirrer device, also has the advantage that the addition of fluoride-trapping agents (cf. R. Lorentz in "Werkstoffe und Korrosion" September 1983, Inhibition des Säureangriffs auf Chemieemail ["Materials and Corrosion" September 1983, Inhibition of attack by acid on chemical enamel]), which moreover are limited in their activity in aqueous, acid solutions, can be dispensed with. Both the material costs for these unproductive additions and the process problems, which as a rule are not to be ignored and arise in particular during the removal of the solid precipitates obtained, such as silicon dioxide or calcium fluoride, which are very difficult to filter off, are thus eliminated.

Turning now to the Drawing, apparatus 10 comprises a container 11, a stirrer 13 (which includes a stirring shaft 15 and a long hollow tube 17 made of carbon fiber-reinforced carbon and containing stirrer blades 18), and a device 21 for monitoring the progress of the reaction. The reaction mixture 19 typically contains at least 1 ppm of fluoride ions and is at a pH below 7. A vapor space 23 above reaction mixture 19 typically contains hydrofluoric acid.

The following examples illustrate the process without limiting it.

EXAMPLE 1

Preparation of 2,3,4,5-Tetrafluorobenzoic Acid 3.4 g of calcium hydroxide and 27.0 g of crude octafluorobisphthalimide (85.5% strength) were suspended in 120 g of water and 6.0 g of 96% strength sulfuric acid.

The mixture was introduced into a 0.75 l Hastelloy® C4 autoclave, in which a stirrer had been incorporated. The stirrer comprised a 22 cm long hollow tube (external diameter 2 cm) made of carbon fiber-reinforced carbon (SIGRABON D from SGL Carbon). The tube was provided with 3 notches along the stirrer axis (each displaced by 90°), into which in each case 1 stirrer blade of the same material (size 3 cm high, 6 cm wide) was inserted at right angles and fixed with PTFE tape (cross-beam stirrer). The stirrer shaft was attached to the drive (stainless steel 1.4571) with pins of Hastelloy C4 and sealed off with Asplit FN. The stirrer was operated at a speed of rotation of 200 rpm. The mixture was heated at 160° C. in a PTFE autoclave for 12 hours in the presence of a material specimen of enamel fixed to the stirrer by means of PTFE tape. When the reaction time had ended, the enamel coating on the specimen had been removed completely, that is to say the specimen was completely destroyed. The reaction proved to be complete, according to monitoring by GC, and the mixture was analyzed via a calibrated GC. 17.7 g (91 mmol, 86.2%) of 2,3,4,5-tetrafluorobenzoic acid, which was further processed directly, were detected.

A specimen of V4A steel (material No. 1.4571) was employed under analogous conditions, the specimen being about half in the gas space and half in the liquid space. At the end of the reaction, it was found that the lower part of the specimen was almost completely missing, and the part employed in the gas space showed severe removal of material, pitting corrosion and stress corrosion cracking.

If graphite blocks of the materials Diabon from SGL Carbon, filled with phenol-formaldehyde resin, NS2, fine-grained variant, NS 1 and NS 2 were employed as potential container material under the same conditions for 200 hours, no chemical attack and also no loss in mechanical resistance were to be found. Like the carbon components tested, the stirrer showed no changes at all under these conditions, and in particular also the stirrer blades of the cross-beam stirrer construction showed no changes.

EXAMPLE 2

Preparation of 5-Fluoro-2-Nitrophenol

In this example, the stirrer described in Example 1 was introduced via an axial face seal into an otherwise commercially available PTFE reactor, the axial face seal being made of α-silicon carbide. Instead of Asplit FN, Asplit CN and, as the shaft material, CFP (carbon fiber-reinforced plastic based on phenolic resin) were employed. 119.4 g (0.75 mol) of 2,4-difluoronitro-benzene were initially introduced into the PTFE reactor, 104.8 g (1.566 mol) of potassium hydroxide (85% strength) in 300 g of water were added dropwise at 55° C. in the course of 4 hours, and the temperature was then increased to 60° C. Specimens (stainless steel V4A) of material No. 1.4571 were positioned in the liquid and in the vapor space. After the end of the reaction, 96% strength sulfuric acid was added until pH 2.3 was reached and, as a fluoride-trapping agent, 40 g of highly disperse silicic acid (Aerosil®) and 38.0 g of calcium hydroxide were added, a pH of 4.2 being established. Introduction of steam was started, after which 5-fluoro-2-nitrophenol was distilled off with the steam. During the steam distillation, the pH was reduced to 1.5 in the course of 1.5 hours by means of 96% strength sulfuric acid, and was then kept at this value. The distillate was cooled to 10° C. and then filtered. 91.9 g (0.58 mol, 78%) of 5-fluoro-2-nitrophenol were obtained as a yellow solid. After the experiment had been repeated several times, the stirrer proved to be unchanged. Specimens of materials 1.4462 and 1.4539 showed uniform attack (integral rates of removal of material of between 1 and 6 mm/a) and partial pitting corrosion and stress corrosion cracking after an exposure time of only 50 hours.

EXAMPLE 3

Preparation of 2,6-Difluorobenzoic Acid from 2,6-Difluorobenzonitrile 139 g (1 mol) of 2,6-difluorobenzonitrile were introduced into 235 g of 75% strength sulfuric acid in a PTFE reactor of the configuration described in Example 2 at 20° C. and the mixture was covered with a layer of nitrogen. It was heated to 150° C. in the course of 1 hour and then kept at 150° C. for 6 hours. After this time, the mixture was cooled and poured onto 750 g of ice-water and the product which had precipitated out was isolated by filtration and subsequent washing with water (3 times with 200 g each time) and subsequently dried. 137 g (86.7%, 0.867 mol) of colorless 2,6-difluorobenzoic acid were obtained as a powder. The nature of the material of the stirrer was checked after 10 batches and proved to be unchanged.

We claim:

1. A process for preparing or working up fluorine containing compounds in an apparatus constructed and arranged to prevent fluorine induced corrosion, the fluorine containing compounds including fluorinated aromatic carboxylic acids or fluorinated phenols, the process comprising reacting or working-up a reaction mixture in the apparatus, wherein the reaction mixture includes organic compounds selected from the group consisting of nitriles, amides, anhydrides, esters, carboxylic chlorides, imides, and benzotrihalides such that at least one of the organic compounds contains a fluorine atom, and wherein the apparatus comprises a container and a stirrer, the stirrer comprising a carbon material selected from the group of corrosion-resistant materials consisting of corrosion-resistant electrographite, carbon fiber-reinforced plastic, and carbon fiber-reinforced carbon.

2. The process as claimed in claim 1, wherein the reaction mixture proceeds through a reaction type selected from the group consisting of halogen exchange, decarboxylation, decarbonylation, and hydrolysis.

3. A fluorinated acid or fluorinated phenol prepared from the process as claimed in claim 1.

4. An apparatus resistant to fluorine induced corrosion from fluorine containing compounds in a reaction mixture, the fluorine containing compounds including fluorinated aromatic carboxylic acids or fluorinated phenols, wherein the reaction mixture includes organic compounds selected from the group consisting of nitrites, amides, anhydrides, esters, carboxylic chlorides, imides, and benzotrihalides such that at least one of the organic compounds contains a fluorine atom, and wherein the apparatus comprises a container and a stirrer, the stirrer comprising a carbon material selected from the group of corrosion-resistant materials consisting of corrosion-resistant electrographite, carbon fiber-reinforced plastic, and carbon fiber-reinforced carbon.

5. The process as claimed in claim 1, wherein the container also comprises a carbon material or is lined with this material.

6. The process as claimed in claim 1, wherein the stirrer and container are sealed off by at least one material filled with epoxy, melamine, furan, alkyd, vinyl, polyester, urethane or phenolic resin.

7. The process as claimed in claim 1, wherein said apparatus has sealing points on a said stirrer and on the container, and said sealing points are protected by layers of inert material.

8. The process as claimed in claim 1, wherein said reacting step is carried out at a temperature within the range of −20° to 220° C.

9. The process as claimed in claim 1, which is carried out under 0.05 to 4 MPa.

10. The process as claimed in claim 1, wherein said reaction mixture contains reactants for forming a fluorinated aliphatic carboxylic acid, a fluorinated aromatic carboxylic acid, or a fluorinated hydroxy compound, and a said acid or a said hydroxy compound is recovered as the reaction product.

11. The process as claimed in claim 1, wherein said reaction mixture is maintained at a pH below 7 and contains at least 1 ppm of fluoride ions and optionally further halide ions.

12. The process as claimed in claim 1, wherein said container contains a vapor space as well as the reaction mixture; wherein said reaction mixture contains hydrofluoric acid or an aqueous medium or a mixture thereof; and wherein, during said reacting step, hydrofluoric acid is optionally present in the vapor space.

13. The process as claimed in claim 1, wherein the reaction medium comprises a non-oxidizing medium.

14. The process as claimed in claim 7, wherein said layers of inert material comprise a noble metal.

15. The process as claimed in claim 1, wherein said reacting step is carried out at a temperature in the range of 50° to 180° C. and under 0.1 to 2 MPa.

* * * * *

UNITED STATES PATENT AND TRADEMARK OFFICE
CERTIFICATE OF CORRECTION

PATENT NO. : 5,773,651
DATED : June 30, 1998
INVENTOR(S) : Ralf Pfirmann, et. al.

It is certified that error appears in the above-identified patent and that said Letters Patent is hereby corrected as shown below:

Claim 4, line 6 (column 9, line 6), change "nitrites" to --nitriles--.

Signed and Sealed this

Twenty-second Day of September, 1998

Attest:

BRUCE LEHMAN

Attesting Officer

Commissioner of Patents and Trademarks